US007901728B2

(12) United States Patent
Van Sciver et al.

(10) Patent No.: US 7,901,728 B2

(45) **Date of Patent: *Mar. 8, 2011**

(54) CLAMP MANDREL FIXTURE AND A METHOD OF USING THE SAME TO MINIMIZE COATING DEFECTS

(75) Inventors: Jason Van Sciver, Los Gatos, CA (US); Manish Gada, Santa Clara, CA (US); Jessie Madriaga, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/636,301

(22) Filed: Dec. 11, 2009

(65) Prior Publication Data

US 2010/0092655 A1 Apr. 15, 2010

Related U.S. Application Data

(60) Continuation of application No. 11/437,589, filed on May 19, 2006, now Pat. No. 7,648,725, which is a division of application No. 10/319,042, filed on Dec. 12, 2002, now Pat. No. 7,074,276.

(51) Int. Cl.
*A61L 33/00* (2006.01)

(52) U.S. Cl. ..... 427/2.1; 427/2.24; 427/2.25; 427/421.1; 427/424; 427/425; 427/427.4; 427/427.5

(58) Field of Classification Search .................... 427/2.1
See application file for complete search history.

(56) References Cited

U.S. PATENT DOCUMENTS

| | | | | |
|---|---|---|---|---|
| 1,133,334 | A * | 3/1915 | Strycker et al. | 269/6 |
| 1,333,334 | A | 3/1920 | Strycker | |
| 1,346,584 | A | 7/1920 | Angle | |
| 3,226,245 | A | 12/1965 | Dettling et al. | |
| 5,716,981 | A * | 2/1998 | Hunter et al. | 514/449 |

* cited by examiner

*Primary Examiner* — Michael Barr
*Assistant Examiner* — Andrew Bowman
(74) *Attorney, Agent, or Firm* — Squire, Sanders & Dempsey (US) LLP

(57) ABSTRACT

A mounting assembly for supporting a stent and a method of using the same to coat a stent is disclosed.

22 Claims, 5 Drawing Sheets

CLAMP MANDREL FIXTURE AND A METHOD OF USING THE SAME TO MINIMIZE COATING DEFECTS

CROSS-REFERENCE TO RELATED APPLICATIONS

This application is continuation of application Ser. No. 11/437,589 filed May 19, 2006, now U.S. Pat. No. 7,648,725, which is a divisional of application Ser. No. 10/319,042 filed Dec. 12, 2002, now U.S. Pat. No. 7,074,276, the contents of both applications are incorporated herein by reference.

BACKGROUND OF THE INVENTION

1. Field of the Invention

This invention relates to a clamp mandrel fixture for supporting a stent during the application of a coating composition.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral gaps or openings 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is the potential for coating defects. While some coating defects can be minimized by adjusting the coating parameters, other defects occur due to the nature of the interface between the stent and the apparatus on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the needed coating from the stent and leaving bare areas. Alternatively, the excess coating may stick to the stent, thereby leaving excess coating as clumps or pools on the struts or webbing between the struts.

Thus, it is desirable to minimize the interface between the stent and the apparatus supporting the stent during the coating process to minimize coating defects. Accordingly, the present invention provides for a device for supporting a stent during the coating application process. The invention also provides for a method of coating the stent supported by the device.

SUMMARY

A device for supporting a stent during the application of a coating substance to the stent is provided. In one embodiment, the device comprises a base, a mandrel extending from the base for penetrating at least partially through the longitudinal bore of the stent, and clamp elements extending from the base, the clamp elements configured to have an open configuration for allowing the mandrel to be inserted into the longitudinal bore of the stent, and a closed configuration for securing the stent on the mandrel during the application of the coating substance to the stent.

The outer diameter of the mandrel can be smaller than the inner diameter of the stent. In one variation, the base can include an indented portion, wherein each of the clamp elements can include a first segment extending over the indented portion of the base and a second segment extending out from the base such that an application of a force to the first segments of the clamp elements over the indented portion of the base causes the second segments to move away from each other towards the open configuration and the release of the force results in the second segments of the clamp elements to retract back towards each other. In the closed configuration, the clamp elements can compress against the mandrel. In one embodiment, each of the clamp elements includes a first segment having a first length and a second segment having a second length, shorter than the first length, the second segments being bent in an inwardly direction towards the mandrel for engagement with the mandrel when the clamp elements are in the closed configuration. The first segments does not contact the stent when the clamp elements are in the closed configuration. Moreover, the stent should not be capable of contacting the base when the stent is secured by the clamp elements on the mandrel.

In accordance with another embodiment, the device comprises a mandrel capable of extending at least partially through the hollow body of a stent, and an arm element for extending through a gaped region between the struts of the stent for holding the stent on the mandrel during the application of a coating composition to the stent. In one embodiment, the device additionally includes a base member, wherein the mandrel extends from a center region of an end of the base member and the arm element extends from an edge of the end of the base member. The arm element can be characterized by a generally "L" shaped configuration having a long segment and a short segment. The long segment of the arm element can be generally parallel to the mandrel and the short segment of the arm element can be generally perpendicular to the mandrel, the short segment of the arm being configured to extend through the gaped region of the stent to compress against the mandrel. In one variation, the diameter of the mandrel plus the length of the short segment of the arm element is greater than the outer diameter of the stent so as to prevent the stent from making contact with the long segment of the arm element during the application of the coating composition. The long segment of the arm element is capable of flexibly bending for engaging and disengaging the short segment of the arm element from the mandrel. In one embodiment, in a natural position, the long segment of the arm element is in a generally linear configuration allowing the short segment of the arm element to be compressed against the mandrel. In another embodiment, the length of the mandrel as measured from the end of the base member is longer than the length of the long segment of the arm element as measured from the end of the base member.

In accordance with yet another embodiment of the invention, a system for supporting a stent during the application of a coating substance to the stent is provided. The system comprises a base member and a first clamp member and a second clamp member extending from the base member, wherein a segment of each clamp member is configured to penetrate into a gaped region of a scaffolding network of the stent for supporting the stent on the base member during the application of the coating substance. In one embodiment, a motor assembly is connected to the base member for rotating the stent about the longitudinal axis of the stent during the application of the coating substance. In another embodiment, a mandrel extends from the base member for being inserted through the hollow tubular body of the stent, wherein the segments of the clamp members that are configured to penetrate into the gaped regions of the scaffolding network are configured to engage with the mandrel for securing the stent on the mandrel. The system can also include a nozzle assembly for spraying the coating substance onto the stent.

In accordance with yet another embodiment, a device for supporting a stent during the application of a coating substance to the stent is provided, the device comprises base member having a indented portion and a clamp member having a first segment disposed on the base member and extending over the indented portion of the base member, and a second segment extending out from one end of the base member for engagement with the stent. The application of pressure on a region of the first segment extending over the indented portion of the base member causes the clamp member to extend in an outwardly direction. The device can additionally include a second clamp member having a first segment disposed on the base member and extending over the indented portion of the base member, and a second segment extending out from the one end of the base member for engagement with the stent, wherein the application of a pressure on the first segments of the first and second clamp members causes the second segments of the first and second clamp members to bias away from one another and the release of the pressure from the first segments causes the first and second clamp members to bias towards each other for engagement of the stent.

A method of coating a stent is also provided comprising positioning the stent on any of the embodiment of the support device and applying a coating composition to the stent.

DETAILED DESCRIPTION

Embodiments of the Mounting Assembly

Figure 1:
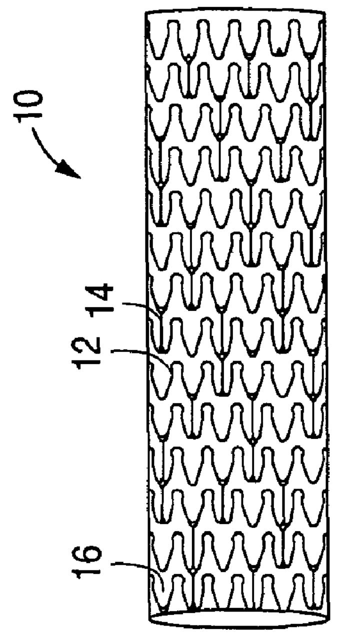
Figure 1 (PRIOR ART)
FIG. 1 illustrates a conventional stent.
Figure 2A:
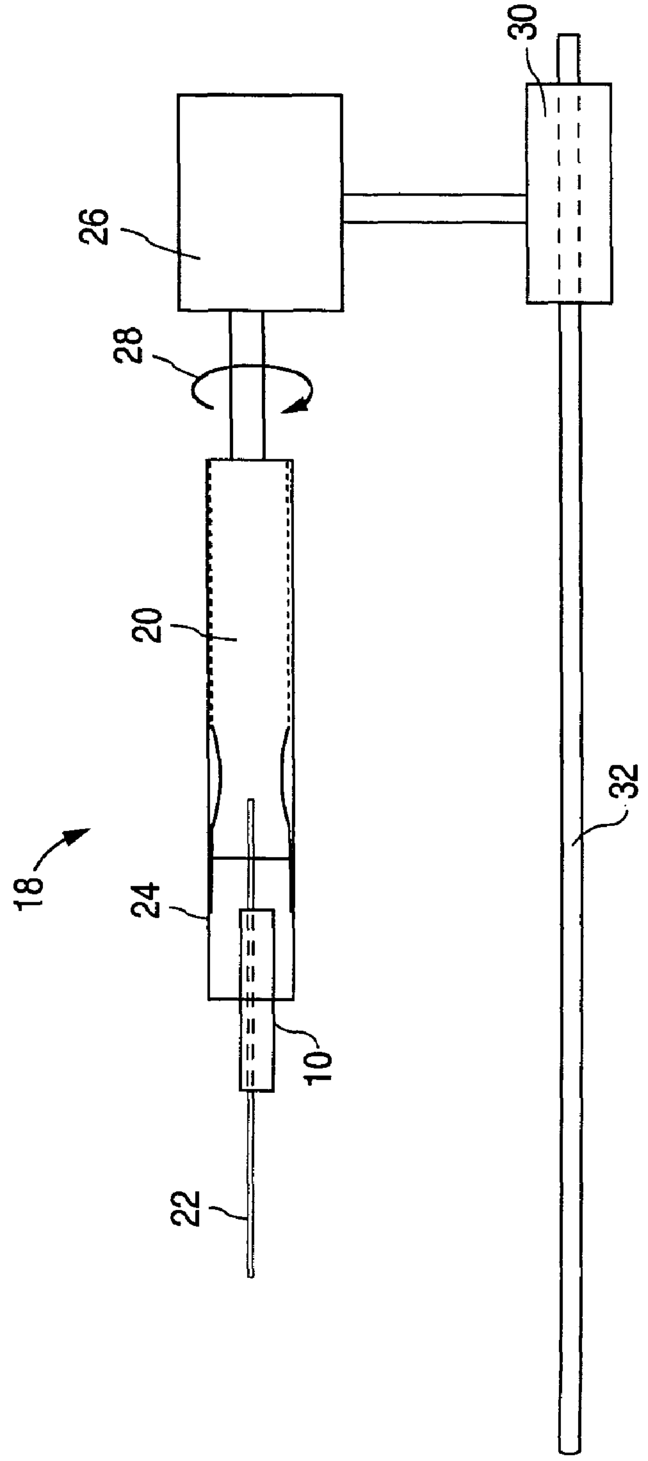
FIG. 2A illustrates a mounting assembly for supporting a stent in accordance with one embodiment of the invention.

Referring to FIG. 2A, a mounting assembly 18 for supporting stent 10 is illustrated to include a base 20, a center pin or mandrel 22, and clamp or arm elements 24. Base 20 can connect to a motor 26, which provides rotational motion to mounting assembly 18, as depicted by arrow 28, during the coating process. Another motor 30 can also be provided for moving mounting assembly 18 and thus stent 10 in a linear direction, back and forth, along a rail 32.

Figure 2B:
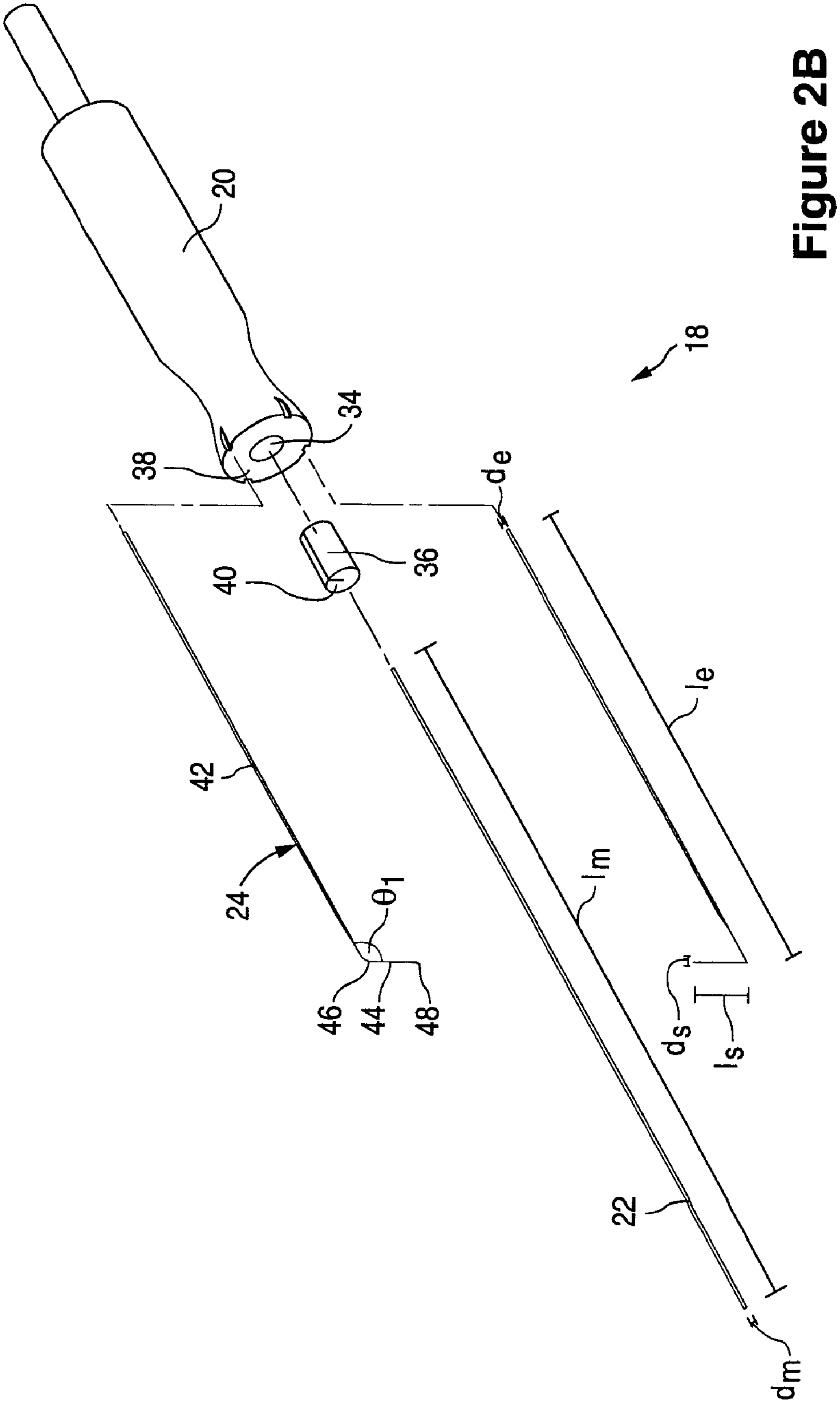
FIG. 2B illustrates an expanded perspective view of the mounting assembly in accordance with one embodiment of the present invention.

Mandrel 22 extends longitudinally from base 20, for example from a central region of the end of base 20. In accordance with one embodiment, mandrel 22 and base 20 can be manufactured as a single component. Alternatively, mandrel 22 and base 20 can be manufactured separately and later coupled to one another. In such an embodiment, base 20 can include a bore 34 for receiving mandrel 22, as illustrated in FIG. 2B. Mandrel 22 can be press fitted into bore 34 or otherwise coupled to base 20 via, for example, welding or adhesives. In the depicted embodiment, mounting assembly 18 additionally includes a mandrel holder 36 for receiving mandrel 22. In such an embodiment, mandrel holder 36 can be permanently or temporarily affixed within bore 34 such that surfaces 38 and 40 are flush upon assembly, and mandrel 22 can be, for example, press fit into mandrel holder 36. A mandrel 22 manufactured separately from base 20 can also be disposable.

Mandrel 22 can be of any suitable diameter $d_m$ and any suitable length $l_m$ that will allow for sufficient support of stent 10 during the coating process. Diameter $d_m$ should be small enough to allow maximum room for motion of stent 10, thereby minimizing the possibility that the inner surface of stent 10 will stick to the outer surface of mandrel 22 during the coating process. Diameter $d_m$ should be large enough to provide sufficient support to stent 10 during rotation as well as against any downward forces exerted during the spraying and drying cycles of the coating process. Length $l_m$ should be longer than the length of stent 10 such that mandrel 22 extends beyond the mounted stent 10 at each of its opposing ends. By way of example and not limitation, mandrel 22 can have diameter $d_m$ that is about 20% of the inner diameter of stent 10 and length $l_m$ that is about ⅛ inch longer than the length of stent 10.

Mandrel 22 can be of any material that is capable of supporting stent 10 and that is compatible with the particular coating composition to be applied to stent 10. For example, mandrel 22 can be made of stainless steel, graphite or a composite. In another embodiment, mandrel 22 can be made of nitinol, the super-elastic properties of which allow mandrels 22 of very small diameters $d_m$ to maintain suitable strength and flexibility throughout the coating process.

Mounting assembly 18 is illustrated as having two arms or clamp elements 24 spaced 180° apart and extending from the and edge of the end of the base 20. In commercially useful embodiments, any number of arms 24 in any configuration can be used to adequately support stent 10, and the embodiments of the present invention should not be limited to a mounting assembly 18 having two arms 24 spaced 180° apart as illustrated in the Figures. It should be noted, however, that the more arms 24 employed to support stent 10, the more contact points that exist between mounting assembly 18 and stent 10. In addition, although each arm 24 is depicted in the Figures as a separate component, multiple arms 24 can be formed from a single component. For example, a wire can be bent into a U-shape such that one half of the wire functions as a first arm 24 and the other half of the wire functions as a second arm 24.

Each arm 24 includes an extension portion 42 extending into a support portion 44 at an angle $\phi_1$ via an elbow 46. Angle $\phi_1$ can be at 90 degrees, for example. Extension portion 42 can couple arm 24 to base 20. Arm 24 can be permanently or temporarily affixed to base 20. Support portion 44 extends through opening 16 between struts 12 of mounted stent 10 to facilitate transient contact between mounting assembly 18 and stent 10 during the coating process.

Extension and support portions 42 and 44 of arms 24 can be of any suitable dimensions. Extension portion 42 should have a length $l_e$ suitable to allow positioning of support portion 44 within a preselected opening 16 between struts 12 along mounted stent 10. Although extension portions 42 are illustrated as having the same length $l_e$, extension portions 42 on the same mounting assembly 18 can have different lengths $l_e$ such that their respective support portions 44 are staggered along the length of mounted stent 10. Length $l_s$ of support portions 44 should be such that support tips 48 touch or compress against mandrel 22 when stent 10 is mounted thereon. Support portions 44 that are too short may cause mounted stent 10 to slip off mounting assembly 18 during the coating process, while support portions 44 that are too long run may hinder movement of stent 10 during the coating process. A diameter $d_e$ of extension portion 42 and a diameter $d_s$ of support portion 44 should be capable of providing sufficient support to stent 10 during rotation as well as against any downward forces exerted during the spraying and drying cycles of the coating process while allowing sufficient movement of stent 10 to prevent permanent contact points between arms 24 and stent 10. In one embodiment, diameter $d_e$ of extension portion 42 tapers into a smaller diameter $d_s$ of support portion 44, thereby optimizing both support and movement of mounted stent 10.

As with mandrel 22 discussed above, arms 24 can be of any material that is capable of supporting stent 10 and that is compatible with the particular coating composition to be applied to stent 10. The material of which arms 24 are formed should also be sufficiently flexible to allow bending into a suitable shape as well as to facilitate easy loading and unloading of stent 10.

Arms 24 must be capable of opening and closing about mandrel 22 to facilitate loading and unloading of stent 10. Arms 24 can be opened and closed in any suitable manner. For example, in one embodiment, arms 24 can be manually pulled open and pushed closed by an operator. In another embodiment, arms 24 can be opened by, for example, sliding a ring along arm 24 toward base 20 and can be closed by sliding the ring along arm 24 toward support portion 44.

Figure 3A:
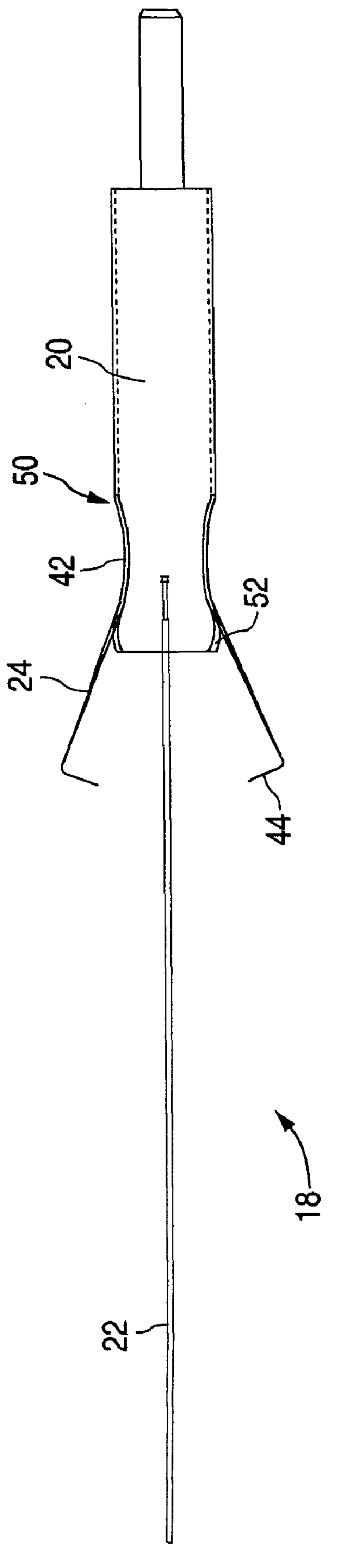
FIG. 3A illustrates the clamp elements or arms of the mounting assembly in an open position in accordance with one embodiment of the present invention.
Figure 3B:
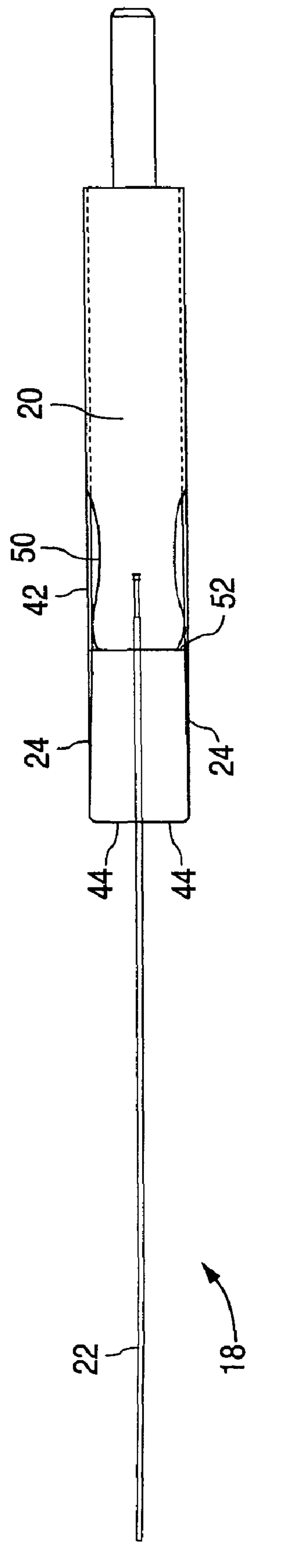
FIG. 3B illustrates the clamp elements or arms of the mounting assembly in a closed position in accordance with one embodiment of the present invention.

FIGS. 3A and 3B illustrate an embodiment in which arms 24 function together as a clamp to facilitate opening and closing. In such an embodiment, base 20 includes an indented portion 50 over which arms 24 extend. Pinching in extension portions 42 over indented portion 50 can open arms 24. Lip 52 further allows extension portions 42 to flexibly spread apart. When pressure is released, extension portions 42 collapse back into a pinched configuration. In this embodiment, the natural position of extension portions 42 should be generally linear and parallel to that of mandrel 22 to allow the biasing of support portion 44 on mandrel 22. The hourglass design of base 20 depicted in the Figures allows an operator to control the opening and closing of clamp-like arms 24 with one hand.

Although mounting assembly 18 is illustrated such that arms 24 are attached to base 20, arms 24 can also be attached to mandrel 22 such that base 20 is not required. In other commercially useful embodiments, mandrel 22 can be supported at its free end during the coating process in any suitable manner. Such support may help mounted stent 10 rotate more concentrically and may also help prevent a slight bend at the free end of mandrel 22 that may otherwise occur due to any downward forces exerted during the spraying and drying cycles of the coating process. In one such embodiment, the free end of mandrel 22 can be stabilized by allowing the free end to rest in a holder such as, for example, a V-block. In another embodiment, a second rotatable base can be coupled to the free end of mandrel 22. The second base can be coupled to a second set of arms. In such an embodiment, at least one base 20 should be disengagable from mandrel 22 so as to allow loading and unloading of stent 10.

Loading a Stent onto the Mounting Assembly

The following description is being provided by way of illustration and is not intended to limit the embodiments of mounting assembly 18, the method of loading stent 10 onto mounting assembly 18, or the method of using mounting assembly 18 to coat stent 10. Referring again to FIG. 3A, clamp-like arms 24 of mounting assembly 18 can be opened by pinching extension portions 42 of arms 24 at depression 50 in the hourglass-shaped base 20 to cause support portions 44 of arms 24 to spread apart. Stent 10 can then be loaded onto mandrel 22 by, for example, holding mounting assembly 18 at an angle (e.g., 15° from horizontal) and sliding stent 10 over mandrel 22 toward base 20. Clamp-like arms 24 can be closed about stent 10 by releasing the pressure applied to extension portions 42, as depicted in FIG. 3B.

Figure 4:
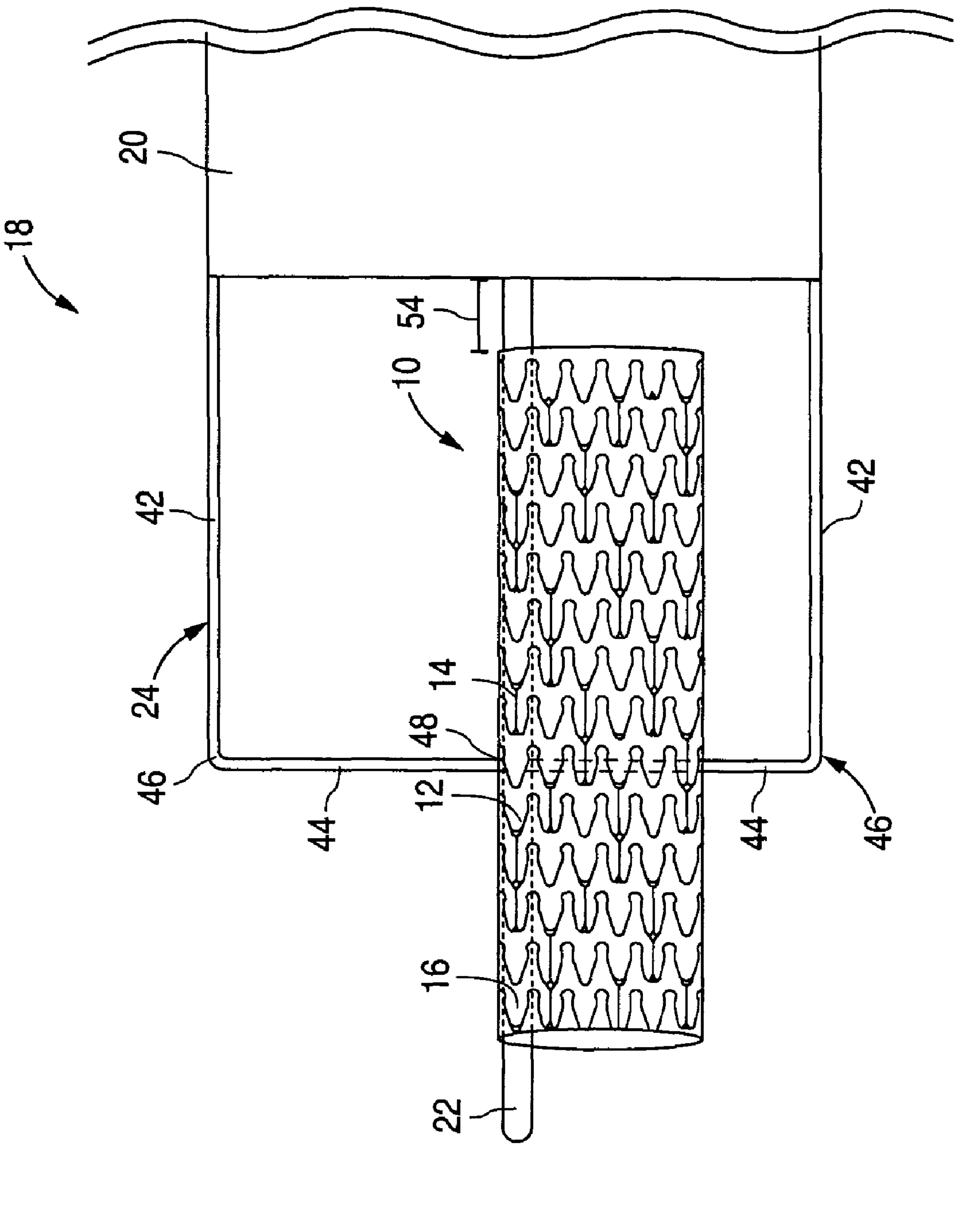
FIG. 4 is a magnified view of the interface between the mounting assembly and the stent in accordance with one embodiment of the present invention.

FIG. 4 depicts the interface between a properly mounted stent 10 and mounting assembly 18. Support portions 44 of arms 24 should protrude through openings 16 between struts 12 of stent 10, and support tips 48 of support portions 44 should touch or compress against mandrel 22. As illustrated, mounted stent 10 should not touch base 20. A gap 54 between base 20 and stent 10 should be maintained to minimize the number of contact points between mounting assembly 18 and stent 10 as well as to maximize the movement of stent 10 during rotation. By way of example and not limitation, gap 54 can be about 1 mm to about 5 mm for stent 10 that is 13 mm to 38 mm long and about 1 mm to about 9 mm for stent 10 that is about 8 mm long. Additionally, as best illustrated by the Figures, diameter $d_m$ of mandrel plus length $l_s$ of support portion 44 should be greater than the outer diameter of stent 10 to prevent stent 10 from contacting extension portions 42.

Figures 5A, 5B, 5C:
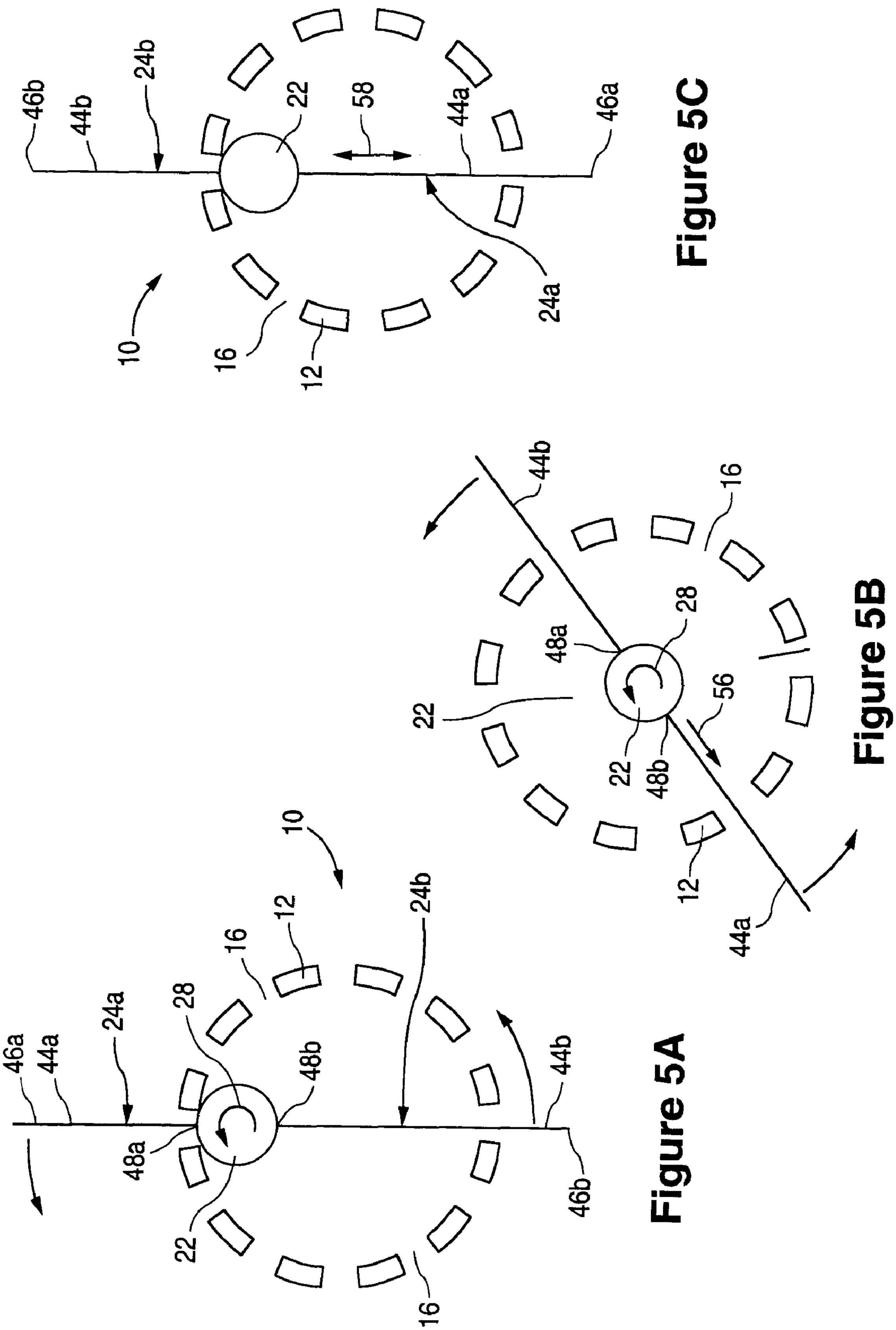
FIGS. 5A-5C are end views illustrating the interface between the mounting assembly and the stent upon rotation during the coating process in accordance with one embodiment of the present invention.

FIGS. 5A-5C illustrate the moving interface between a properly mounted stent 10 and mounting assembly 18 having two arms 24*a* and 24*b* spaced 180° apart upon rotation of mounting assembly 18. As depicted in FIG. 5A, support portions 44*a* and 44*b* of arms 24*a* and 24*b*, respectively, protrude through openings 16 between struts 12 of stent 10, and support tips 48*a* and 48*b* flush against mandrel 22. As mandrel 22 is rotated in the direction of arrow 28, which can be either clock-wise or counter clock-wise, mounted stent 10 also rotates in the direction of arrow 28. As arms 24*a* and 24*b* approach the vertical position, stent 10 slides downward along support portions 44*a* and 44*b* in the direction of arrow 56, as depicted in FIG. 5B, until arms 24*a* and 24*b* reach the vertical position depicted in FIG. 5C upon rotation one half-turn or 180°. Continued rotation of mandrel 22 allows stent 10 to move back and forth along support portions 44*a* and 44*b* between elbows 46*a* and 46*b* in the direction of double arrow 58 depicted in FIG. 5C. Such constant back and forth movement of stent 10 along support portions 44 upon rotation of mandrel 22 during the coating process allows the contact points between stent 10 and mounting assembly 18 to be transient rather than permanent, thereby preventing the coating material from flowing, wicking, collecting, and solidifying at or between arms 24 and stent 10. In some embodiments, the back and forth motion of stent 10 along arms 24 is enhanced by downward forces exerted throughout the coating process by atomization airflow during the spraying cycle and/or dryer airflow during the drying cycle.

Coating a Stent Using the Mounting Assembly

The following method of application is being provided by way of illustration and is not intended to limit the embodiments of the present invention. A spray apparatus, such as EFD 780S spray device with VALVEMATE 7040 control system (manufactured by EFD Inc., East Providence, R.I.), can be used to apply a composition to a stent. EFD 780S spray device is an air-assisted external mixing atomizer. The composition is atomized into small droplets by air and uniformly applied to the stent surfaces. The atomization pressure can be maintained at a range of about 5 psi to about 20 psi, for example 15 psi. The droplet size depends on such factors as viscosity of the solution, surface tension of the solvent, and atomization pressure. Other types of spray applicators, including air-assisted internal mixing atomizers and ultrasonic applicators, can also be used for the application of the composition. The solution barrel pressure can be between 1 to 3.5 psi, for example 2.5 psi. The temperature of the nozzle can adjusted to a temperature other than ambient temperature during the spray process by the use of a heating block or other similar devices. For example, the temperature of the nozzle can be between 45° to about 88°, the temperature depending on a variety of factors including the type and amount of polymer, solvent and drug used. The nozzle can be positioned at any suitable distance away form the stent, for example, about 10 mm to about 19 mm.

During the application of the composition, mandrel 22 can be rotated about its own central longitudinal axis. Rotation of mandrel 22 can be from about 10 rpm to about 300 rpm, more narrowly from about 40 rpm to about 240 rpm. By way of example, mandrel 22 can rotate at about 100 rpm. Mandrel 22 can also be moved in a linear direction along the same axis. Mandrel 22 can be moved at about 1 mm/second to about 6 mm/second, for example about 3 mm/second, or for at least two passes, for example (i.e., back and forth past the spray nozzle). The flow rate of the solution from the spray nozzle can be from about 0.01 mg/second to about 1.0 mg/second, more narrowly about 0.1 mg/second. Multiple repetitions for applying the composition can be performed, wherein each repetition can be, for example, about 1 second to about 10 seconds in duration. The amount of coating applied by each repetition can be about 0.1 micrograms/$cm^2$ (of stent surface) to about 40 micrograms/$cm^2$, for example less than about 2 micrograms/$cm^2$ per 5-second spray.

Each repetition can be followed by removal of a significant amount of the solvent(s). Depending on the volatility of the particular solvent employed, the solvent can evaporate essentially upon contact with the stent. Alternatively, removal of the solvent can be induced by baking the stent in an oven at a mild temperature (e.g., 60° C.) for a suitable duration of time (e.g., 2-4 hours) or by the application of warm air. The application of warm air between each repetition prevents coating defects and minimizes interaction between the active agent and the solvent. The temperature of the warm air can be from about 30° C. to about 85° C., more narrowly from about 40° C. to about 55° C. The flow rate of the warm air can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The blower pressure can be, for example between 10 to 35 psi, more narrowly 12 to 15 psi and can be positioned at a distance of about 10 to 20 mm away from the stent. The warm air can be applied for about 3 seconds to about 60 seconds, more narrowly for about 10 seconds to about 20 seconds. By way of example, warm air applications can be performed at a temperature of about 50° C., at a flow rate of about 40 CFM, and for about 10 seconds. Any suitable number of repetitions of applying the composition followed by removing the solvent(s) can be performed to form a coating of a desired thickness or weight. Excessive application of the polymer in a single application can, however, cause coating defects.

Operations such as wiping, centrifugation, or other web clearing acts can also be performed to achieve a more uniform coating. Briefly, wiping refers to the physical removal of excess coating from the surface of the stent; and centrifugation refers to rapid rotation of the stent about an axis of rotation. The excess coating can also be vacuumed off of the surface of the stent.

In accordance with one embodiment, the stent can be at least partially pre-expanded prior to the application of the composition. For example, the stent can be radially expanded about 20% to about 60%, more narrowly about 27% to about 55%—the measurement being taken from the stent's inner diameter at an expanded position as compared to the inner diameter at the unexpanded position. The expansion of the stent, for increasing the interspace between the stent struts during the application of the composition, can further prevent "cob web" formation between the stent struts.

In accordance with one embodiment, the composition can include a solvent and a polymer dissolved in the solvent. The composition can also include active agents, radiopaque elements, or radioactive isotopes. Representative examples of polymers that can be used to coat a stent include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

The active agent can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere® , from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be appropriate include alpha-interferon, genetically engineered epithelial cells, rapamycin and dexamethasone. Exposure of the active ingredient to the composition should not adversely alter the active ingredient's composition or characteristic. Accordingly, the particular active ingredient is selected for compatibility with the solvent or blended polymer-solvent.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for supporting a stent during a stent coating process, comprising:
- positioning a stent on an apparatus comprising:
  - a first arm element; and
  - a second arm element, wherein one or both of the first and second arm elements can be pivoted from a first position to a second position so as to have a first angle between the first and second arm elements for supporting the stent and pivoted from the second position to the first position so as to have a second angle between the first and second arm elements for releasing of the stent; and
- applying a coating material to the stent, wherein the positioning comprises moving a tip of the first arm element through a lateral gap between struts of the stent, and the tip of the first arm element is disposed within a longitudinal bore of the stent during the applying of the coating material.

2. The method of claim 1, wherein the first and second arm elements are coupled to a base member.

3. The method of claim 1, wherein at least one of the first and second arm elements are coupled to a mandrel, the mandrel configured to penetrate at least partially in the longitudinal bore of the stent.

4. The method of claim 1, additionally comprising a third arm element positioned between the first and second arm elements, wherein when the stent is in a support position, the first and second arm elements are in contact with the third arm element.

5. The method of claim 1, wherein the second angle is greater than the first angle.

6. A method for supporting a stent during a stent coating process, comprising:
- positioning a stent on an apparatus, comprising:
  - a first arm element; and
  - a second arm element, wherein in a natural configuration, the arm elements are in an engaged configuration with the stent and wherein with an application of a force, the arm elements can be biased relative to each other for disengagement of the stent; and
- applying a coating material to the stent, the positioning comprises moving a tip of the first arm element through a lateral gap between struts of the stent, and the tip of the first arm element is disposed within a longitudinal bore of the stent during the applying of the coating material.

7. The method of claim 6, wherein the first and second arm elements are coupled to a base element.

8. The method of claim 6, wherein at least one of the first and second arm elements are coupled to a mandrel, the mandrel configured to penetrate at least partially in the longitudinal bore of the stent.

9. The method of claim 6, wherein the stent comprises frame elements and openings in the frame elements and engaged is defined as penetration into opening(s) of the frame elements.

10. The method of claim 6, additionally comprising a third arm element positioned between the first and second arm elements, wherein in the engaged configuration, the first and second arm elements contact the third arm element.

11. A method for supporting a stent during a coating process, comprising supporting the stent on:

a first member; and a second member capable of bending between a first position and a second position so as to allow the stent to be releasably supported by the first and second members; and applying a coating material to the stent while the second member passes through a lateral gap between struts of the stent.

12. The method of claim 11, wherein the first member is capable of being inserted at least partially through a longitudinal bore of the stent.

13. The method of claim 11, wherein the first member is capable of bending between a first position and a second position.

14. The method of claim 11, wherein the first and second members extend from a base member.

15. The method of claim 11, wherein the second member makes contact with the first member when the stent is being supported by the device.

16. The method of claim 11, wherein the first member is configured to be disposed within a bore of the stent.

17. The method of claim 11, wherein the first member is capable of bending between a first position and a second position and wherein the first and second members are configured to penetrate into gaps between the struts of the stent.

18. The method of claim 11, wherein the second member comprises a non-linear arm element.

19. The method of claim 11, wherein a length of the second member is shorter than a length of the first member.

20. The method of claim 1, wherein the positioning further comprises moving a tip of the second arm element through the longitudinal bore of the stent or through another lateral gap between the struts of the stent.

21. The method of claim 6, wherein the positioning further comprises moving a tip of the second arm element through the longitudinal bore of the stent or through another lateral gap between the struts of the stent, and wherein the tip of the second arm element is disposed within the longitudinal bore of the stent during the applying of the coating material.

22. The method of claim 11, wherein during the applying of the coating material to the stent, the first arm member passes through a longitudinal bore of the stent or through a second lateral gap between the struts of the stent.

* * * * *